United States Patent
Aime et al.

(10) Patent No.: US 12,226,494 B2
(45) Date of Patent: Feb. 18, 2025

(54) PHARMACEUTICAL COMPOSITIONS COMPRISING Gd-COMPLEXES AND POLYARYLENE ADDITIVES

(71) Applicant: BRACCO IMAGING S.P.A., Milan (IT)

(72) Inventors: Silvio Aime, Turin (IT); Giuseppe Ferrauto, Turin (IT); Eliana Gianolio, Beinasco (IT); Luciano Lattuada, Cassina de' Pecchi (IT); Alessandro Maiocchi, Monza (IT)

(73) Assignee: BRACCO IMAGING S.P.A., Milan (IT)

( * ) Notice: Subject to any disclaimer, the term of this patent is extended or adjusted under 35 U.S.C. 154(b) by 224 days.

(21) Appl. No.: 17/414,508

(22) PCT Filed: Dec. 17, 2019

(86) PCT No.: PCT/EP2019/085493
§ 371 (c)(1),
(2) Date: Jun. 16, 2021

(87) PCT Pub. No.: WO2020/127154
PCT Pub. Date: Jun. 25, 2020

(65) Prior Publication Data
US 2022/0062444 A1    Mar. 3, 2022

(30) Foreign Application Priority Data
Dec. 18, 2018  (EP) .................................. 18213354

(51) Int. Cl.
*A61K 49/10*    (2006.01)
*A61K 47/20*    (2006.01)

(52) U.S. Cl.
CPC ............ *A61K 49/108* (2013.01); *A61K 47/20* (2013.01)

(58) Field of Classification Search
CPC ..... A61K 49/06; A61K 49/106; A61K 49/108
See application file for complete search history.

(56) References Cited

U.S. PATENT DOCUMENTS

| | | | | |
|---|---|---|---|---|
| 5,514,710 A | * | 5/1996 | Haugland | C07C 309/43 549/453 |
| 6,589,506 B2 | * | 7/2003 | Cremillieux | G01R 33/5601 424/9.364 |
| 2009/0155181 A1 | | 6/2009 | Rowe | |
| 2011/0300070 A1 | * | 12/2011 | Tenstad | A61K 51/088 424/1.73 |

FOREIGN PATENT DOCUMENTS

| | | |
|---|---|---|
| WO | 2004026344 A1 | 4/2004 |
| WO | 2012059576 A1 | 5/2012 |
| WO | 2017098038 A1 | 6/2017 |

OTHER PUBLICATIONS

Diaferia et al., "Peptide Materials Obtained by Aggregation of Polyphenylalanine Conjugates as Gadolinium-Based Magnetic Resonance Imaging Contrast Agents", Adv. Funct. Mater. 2015, 25, 7003-7016 (Year: 2015).*
https://pubchem.ncbi.nlm.nih.gov/compound/pyrene#section=Melting-Point, published from web Mar. 2023 (Year: 2023).*
Ferreira et al. "Ln[DO3A-N-α-(pyrenebutanamido)propionate] complexes: optimized relaxivity and NIR optical properties", Dalton Trans., 2014, 43, 3162-3173 (Year: 2014).*
Aime, S. et al, "Contrast agents for magnetic resonance angiographic applications: 1H and 17O NMR relaxometric investigations on two gadolinium(III) DTPA-like chelates endowed with high binding affinity to human serum albumin," J. Biol. Inorg. Chem., 4:766-774 (1999).
Aime, S. et al, "New paramagnetic supramolecular adducts for MRI applications based on non-covalent interactions between Gd(III)-complexes and beta- or gamma-cyclodextrin units anchored to chitosan," J. Inorg. Biochem, 100:931-938 (2006).
Arena, F. et al, "β-Gal Gene Expression MRI Reporter in Melanoma Tumor Cells. Design, Synthesis, and in Vitro and in Vivo Testing of a Gd(III)Containing Probe Forming a High Relaxivity, Melanin-Like Structure upon β-Gal Enzymatic Activation," Bioconjugate Chem., 22:2625-2635 (2011).
Caravan, P. et al, "Gadolinium(III) Chelates as MRI Contrast Agents: Structure, Dynamics, and Applications," Chem. Rev., 99:2293-2352 (1999).
Dischino, D.D. et al "Synthesis of Nonionic Gadolinium Chelates Useful as Contrast Agents for Magnetic Resonance Imaging. 1,4,7-Tris(carboxymethyl)-10-substituted-1,4,7, 10-tetraazacyclododecanes and Their Corresponding Gadolinium Chelates," Inorg. Chem., 30:1265-1269 (1991).
International Search Report and Written Opinion for PCT/EP2019/085493, mailed Mar. 12, 2020.
Kotek, J. et al., "Synthesis and Characterization of Ligands and their Gadolinium(III) Complexes," In: The Chemistry of Contrast Agents in Medical Magnetic Resonance Imaging, pp. 83-155, John Wiley & Sons, Ltd, Chichester, UK (2013).
Nanni, P. et al, "TS/A: a new metastasizing cell line from a BALB/c spontaneous mammary adenocarcinoma," Clin. Expl. Metastasis, 1:373-380 (1983).

* cited by examiner

*Primary Examiner* — James W Rogers
(74) *Attorney, Agent, or Firm* — VIVICAR Law, PLLC (57) ABSTRACT

The present invention refers to pharmaceutical compositions comprising a macrocyclic gadolinium complex and a water-soluble polyarylene additive useful in diagnostic imaging as diagnostic agents, in particular as contrast agents, specifically in Magnetic Resonance Imaging (MRI).

10 Claims, 9 Drawing Sheets

Figura 3B

PHARMACEUTICAL COMPOSITIONS COMPRISING Gd-COMPLEXES AND POLYARYLENE ADDITIVES

CROSS-REFERENCE TO RELATED APPLICATIONS

This application is the national stage application of corresponding international application number PCT/EP2019/085493, filed Dec. 17, 2019, which claims priority to and the benefit of European application no. 18213354.6, filed Dec. 18, 2018, which is hereby incorporated by reference in its entirety.

TECHNICAL FIELD OF THE INVENTION

The present invention refers to pharmaceutical compositions comprising a macrocyclic gadolinium complex and a water-soluble polyarylene additive useful in diagnostic imaging as diagnostic agents, in particular as contrast agents, specifically in Magnetic Resonance Imaging (MRI).

BACKGROUND OF THE INVENTION

MRI is a non-invasive imaging technology that allows obtaining detailed images of human or animal body organs or tissues.

Images of the human body with the MRI technique originate from the almost ubiquitous presence of water molecules in the body. Signal intensities depend on differences in concentration of water molecules in different tissue as well as on differences in the relaxation times (i.e. longitudinal, $T_1$, and transversal, $T_2$, relaxation times) of water protons located in different environments (i.e. fat vs muscular tissue).

In order to enhance the image contrast, substances can be exploited that shorten the relaxation times of bulk water protons to such an extent that an observable effect is achieved. Such substances are called MRI contrast agents, and typically include a complex of a ligand with a paramagnetic metal ion (as a general reference to MRI imaging and MM contrast agents see, for instance, Caravan, P. et al, *Chem. Rev.* 1999, 99, 2293-2352).

Examples of commercially available MM contrast agents include the complex compound of the $Gd^{3+}$ ion with the DTPA ligand, marketed as MAGNEVIST®; the $Gd^{3+}$ complex of the DTPA-BMA ligand, marketed ad OMNISCAN®; the $Gd^{3+}$ complex of BOPTA, known as gadobenate dimeglumine and marketed as MultiHance™; the $Gd^{3+}$ complex of the DOTA ligand, marketed as DOTAREM®; the $Gd^{3+}$ complex of the hydroxylated tetraaza macrocyclic ligand known as HPDO3A, long time marketed as ProHance® and that of the corresponding butyl-triol derivative, known as Gadobutrol and marketed as Gadovist®.

Preferred MRI contrast agent should display optimal relaxivity.

Relaxivity ($r_{1p}$, $r_{2p}$), expressed in $mM^{-1}s^{-1}$ and usually measured at 298K and 20 MHz (approx. 0.5 T), is the intrinsic property of a paramagnetic complex which characterizes its capability to increase the nuclear magnetic relaxation rate, longitudinal (1/T1) and transverse (1/T2) respectively, of vicinal water protons and, thus, its efficacy as MRI contrast enhancing agent. In general terms, the higher the relaxivity of an MRI contrast agent, the greater its contrast enhancing capability and the stronger the contrast provided in recorded MRI images.

Commercial contrast agents are typically effective at high concentrations (0.1 mM); as a result, there has been a considerable effort to increase their sensitivity. Compounds with high relaxivity can be detected at lower doses, or provide greater contrast at equivalent doses compared to compounds with lower relaxivity.

However, due to the strong expansion of MRI in the medical field, there is still the need of new compounds with improved contrast imaging features, having for instance a good stability and an increased relaxivity allowing to reduce the effective dose of the administered contrast agent.

LIST OF FIGURES

FIG. 3B shows the chemical structure of compounds used as negative references for comparative tests.

LIST OF ABBREVIATIONS

APTS: 8-Aminopyrene-1,3,6 trisulfonic acid
CMPTS: 8-Carboxymethoxypyrene-1,3,6-trisulfonic acid
GBCA: Gadolinium Based Contrast Agent
HBSA: 4-Hydroxybenzenesulfonic acid
HPDS: 6, 8-Dihydroxypyrene-1,3-disulfonic acid
HPTS: 8-Hydroxypyrene-1,3,6-trisulfonic acid
HSA: Human Serum Albumin
MPTS: 8-Methoxy-1,3,6 pyrene trisulfonic acid
MRI: Magnetic Resonance Imaging
2,6 NDS: 2,6 Naphthalene disulphonic acid
1,5 NDS: 1,5 Naphthalene disulphonic acid
PS: 1-Pyrene sulfonic acid
PTS: 1,3,6,8 Pyrenetetrasulfonic acid
SPDS: 6,8-disulfooxypyrene-1,3-disulfonic acid
SPTS: 8-sulfooxypyrene-1,3,6-trisulfonic acid PTS: 1,3,6,8 Pyrentetrasulfonic acid

SUMMARY OF THE INVENTION

The present invention refers to pharmaceutical compositions comprising a macrocyclic gadolinium complex and a water-soluble polyarylene additive.

In a further aspect the invention relates to said pharmaceutical compositions for use as contrast agents, in particular for the diagnostic imaging of a human or animal body, preferably by use of MRI technique.

A further aspect of the invention is a method for the diagnostic imaging of a body organ, tissue or region by use of MRI technique that comprises the use of an effective dose of the pharmaceutical composition of the invention.

In another aspect the invention relates to non-covalent adducts obtainable by the interaction of a macrocyclic gadolinium-based complex with a water-soluble polyarylene additive in an aqueous solution, useful as contrast agents, in particular for the diagnostic imaging of a human or animal body, preferably by use of MRI technique.

According to another aspect, the invention relates to a pharmaceutically acceptable composition comprising at least one adduct according to the invention, or a pharmaceutical salt thereof, in admixture with one or more physiologically acceptable carriers or excipients.

DETAILED DESCRIPTION OF THE INVENTION

It has been surprisingly found that when water-soluble polyarylenes (or polyarylene additives or polyarylene compounds, as herein used interchangeably) are admixed to solutions of macrocyclic gadolinium-based complexes (Gd-complexes) an enhancement of the relaxivity of the Gd-complexes is observed.

An aspect of the present invention is a pharmaceutical composition comprising a macrocyclic gadolinium complex, or a pharmaceutical salt thereof, and a water-soluble polyarylene additive, or a pharmaceutical salt thereof.

Preferred macrocyclic Gd-complexes according to the present invention include complex compounds of tetraazacyclododecan-based chelating ligands with the paramagnetic $Gd^{3+}$ metal ion. Suitable examples include for instance:

Aa

Ab

Ac

Ba

-continued

Bb

Bc and

Aa, Ab and Ac are the active ingredients of commercially available contrast agents known under the trademarks: Pro-Hance (Aa), Gadovist (Ab), Dotarem (Ac).

Ba may be prepared according to the general procedure disclosed in WO 2012059576 by using $GdCl_3$ in place of $YCl_3$.

Bb may be prepared as described in WO 2017/098038.

Bc may be prepared as disclosed in Dischino, D. D. et al, Inorg. Chem. 1991, 30, 1265-1269.

Preferred according to the invention are neutral Gd-complexes; particularly preferred are the complex Ab and Aa, the latter being especially preferred.

A neutral complex according to the present invention is a metal-complex not endowed with any positive or negative residual charge.

Water-soluble polyarylenes according to the invention, useful as suitable additives promoting the enhancement of the relaxivity of the macrocyclic Gd-complex, generally include polyaromatic systems (or polyaromatic compounds, as herein used interchangeably) comprising at least 3, preferably from 3 to 6, more preferably from 3 to 5, most preferably 3 or 4, particularly preferably 4 carbocyclic fused aromatic rings, that are substituted by at least 2, preferably from 3 to 5, more preferably by 3 or 4 hydrophylic substituent groups. The presence of such hydrophilic substituent is generally useful for conferring to the polyarylene additive the desired solubility in water or in a physiologic solution. Suitable hydrophilic substituent groups (capable of promoting the water-solubility of the polyarylene additive) are for instance selected from the group consisting of —OH, —COOH, —SO$_3$H, —OSO$_3$H, —NH$_2$.

According to the present invention, and unless otherwise indicated, the expressions "water soluble" is used with reference to a polyarylene additive, and refers to a compound that has a solubility in water of at least 2 mMol$^{-1}$, preferably equal to, or greater than, 5 mMol$^{-1}$, more preferably than 10 mMol$^{-1}$, and most preferably greater than 20 mMol$^{-1}$. Said additives are used in the form of physiologically acceptable salts, where any of the free acid groups, if present, is converted in the corresponding addition salt with alkali or alkaline-earth metals such as potassium, sodium, calcium or magnesium, or the cations of organic bases comprise, for instance, those of primary, secondary and tertiary amines such as, for instance, ethanolamine, diethanolamine, morpholine, glucamine, N-methylglucamine, N,N-dimethylglucamine.

Preferred anions of inorganic acids, which can be suitably used to prepare salts of the adducts of the invention, comprise the ions of haloacids, for instance chlorides, bromides or iodides, as well as of other suitable ions such as sulfate.

Preferred anions of organic acids comprise those routinely used in pharmaceutical techniques for the salification preparation of salts of basic substances such as, for instance, acetate, succinate, citrate, fumarate, maleate or oxalate.

Preferred cations and anions of amino acids comprise, for instance, those of taurine, glycine, lysine, arginine, ornithine or of aspartic and glutamic acids.

According to a preferred embodiment, the polyarylene additives are selected from the group comprising:

Polyarylene additives according to the invention are commercial available or obtainable according to conventional procedures known to a skilled person.

Interestingly, the addition of these additives to solutions of a macrocyclic gadolinium complex, in particular a tetraazacyclododecan-based gadolinium complex, results in an unexpected enhancement of the relaxivity these complexes display.

Figure 4:
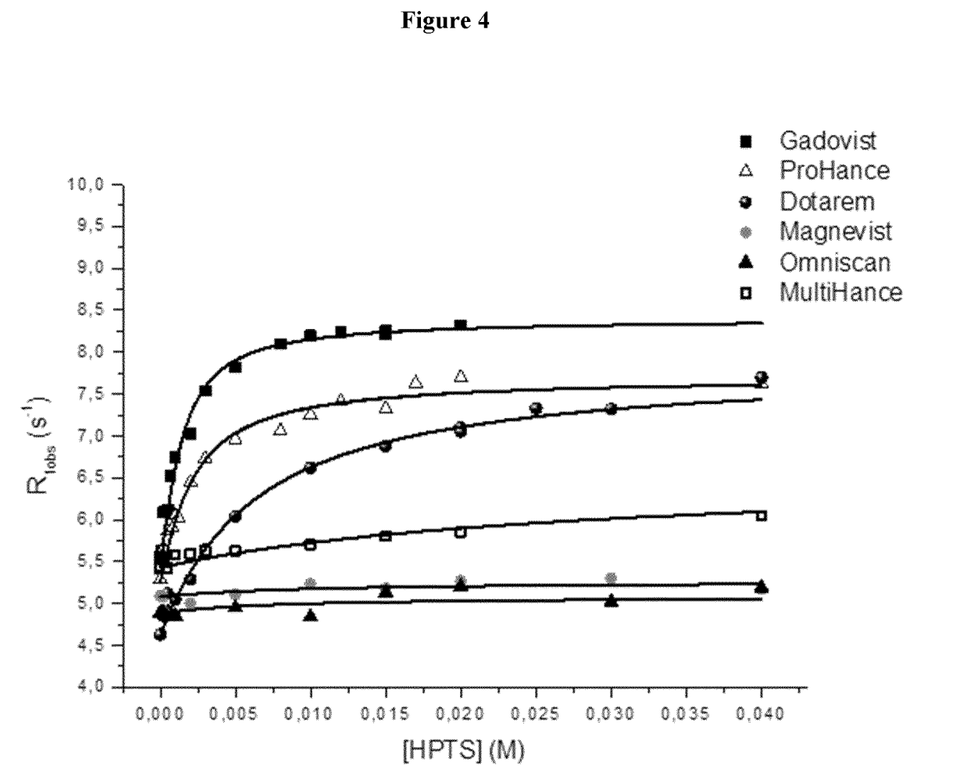
FIG. 4 shows the binding isotherms of commercial Gd-complexes in the presence of increasing amounts of HPTS ([Gd-complex]=1 mM, in Hepes/NaCl, pH=7.0).

As clearly appears from the graph in FIG. 4, greater amounts of polyarylene additive result in higher enhancement of the relaxivity displayed by the Gd complex.

Pharmaceutical compositions according to the present invention include at least one mole of polyarylene additive for each mole of macrocyclic Gd-complex within the solution. In other words, the molar ratio of polyarylene additive to macrocyclic Gd-complex is at least 1:1 (m/m), although greater amount of the polyarylene additive can be used, promoting a greater enhancement of the relaxivity displayed by the gadolinum complex.

Preferably, the molar ratio (m/m) of macrocyclic Gd-complex to polyarylene additive ranges from 1:1 to 1:10, more preferably from 1:1 to 1:5, and most preferably is 1:3.

Interestingly, the relaxivity displayed by the pharmaceutical compositions according to the invention comprising a macrocyclic Gd-complex and a polyarylene additive is at least 10% greater than that of the relevant free Gd-complex. Preferably, the promoted relaxivity increase is of at least 20%, more preferably of at least 30, most preferably of at about 50% of the relaxivity displayed by the free gadolinium complex.

Although not willing to be bound by any particular theory, the Applicant considers that the said observed increase of the relaxivity is ascribable to the formation of a non-covalent adduct of the macrocyclic gadolinium based contrast agent with the water-soluble polyarylene additive.

In the present description, and unless otherwise provided, the expression "adduct" refers to a chemical species AB, each molecular entity of which is formed by direct combination of two separate molecular entities A and B, that are linked to one another through a non-covalent interaction.

Figure 1:
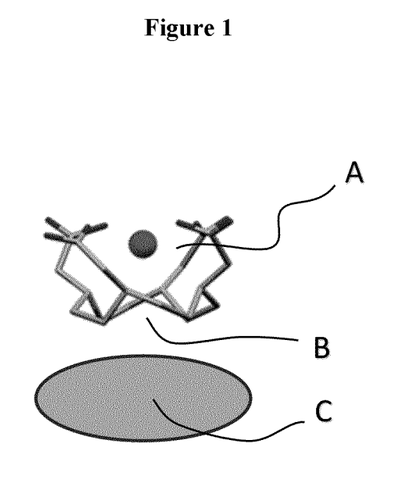
FIG. 1 shows a possible schematic representation of a non-covalent adduct between tetraazacyclododecane-based macrocylic gadolinium complex and a polyarylene additive, where A identifies the hydrophilic portion, and B the lypophilic portion of the Gd-complex, and C identifies the polyarylene.

Still without willing to be bound to any particular theory, it may be supposed a possible non-covalent interaction between the polyarylene compounds and the lipophilic portion (e.g. identified as "B" in FIG. 1, whereas "A" identifies the hydrophilic portion of the Gd-complex while "C" identifies the polyarylene) of a tetraazaciclododecane-based Gd-complexes leading to the formation of a relatively stable adduct by simple admixing the two.

As determined by the Applicant the greater the strength of the non-covalent interaction between the macrocyclic Gd-complex and the polyarylene additive, the lower the amount of polyarylene required to quantitatively promote its conversion into a non-covalent adduct, and the greater the relaxivity increase promoted by the addition of the polyarylene to the Gd-complex.

The strength of the non-covalent binding between the Gd-complex and the polyarylene additive can be quantitatively defined by the association constant (Ka) between the two adduct components.

On the other hand, the attainable increase in relaxivity is ascribable to the relaxivity (Rb) of the resulting adduct. To this extent, the value of both Ka and Rb can be determined, for example, as described, by Aime, S. et al, *J. Biol. Inorg. Chem.* 1999, 4, 766-774 and by Aime, S. et al, *J. Inorg. Biochem.* 2006, 100, 931-938.

Preferred polyarylene additives have an association constant Ka for the macrocyclic Gd-complex within the pharmaceutical composition of at least 250 $M^{-1}$, more preferably of at least 350, even more preferably of at least 450, e.g. particularly preferably of at least 600 $M^{-1}$.

For instance, it has been observed that the addition of three moles of a polyarylene additive with an affinity constant Ka for the macrocyclic Gd-complex of interest of about 600 $M^{-1}$ results in having at least 60% of the latter in the form of an adduct with said polyarylene.

Higher Ka values, e.g. up to $1\times10^7$ $M^{-1}$, are preferred in order to have a relatively rapid and substantially complete conversion of the Gd-complex in the form of adduct with the polyarylene additive (i.e. substantially 100% of the macrocyclic gadolinium complex in the form of an adduct with the polyarylene additive), leading to higher increase of the Gd-complex's relaxivity, e.g. up to 50% in case the Gd-complex is that of ProHance.

Suitable Ka values allowing to obtain about 20%, 60% or 99% of the gadolinium complex in the form of the non-covalent adduct with HPTS are provided in the following Table 1. For instance, the addition of 3 equivalents of HPTS to a solution of a macrocyclic gadolinium complex (GdL), whose affinity for HPTS is of about 89 $M^{-1}$, results in 20% of the complex in the form of an adduct with HPTS. Alternatively, in order to have about 60% of the Gd-based contrast agent (GdL) in the form of a non-covalent adduct with HPTS, a GdL having an affinity for HPTS of about 625 $M^{-1}$, in a 3:1 HPTS/GdL m/m ratio should be used.

For instance, when the Gd-complex is the active ingredient of ProHance (compound Aa defined above), percentages of 20%, 60% or 99% of the complex in the form of a non-covalent adduct with HPTS typically result in an improvement of the relaxivity shown by the free complex of about 10%, 30% or 50% respectively.

TABLE 1

|  | HPTS:GdL = 1:1 | HPTS:GdL = 3:1 | HPTS:GdL = 10:1 |
| --- | --- | --- | --- |
| GdL bound = 20% | 312 $M^{-1}$ | 89 $M^{-1}$ | 25 $M^{-1}$ |
| GdL bound = 60% | 3750 $M^{-1}$ | 625 $M^{-1}$ | 159 $M^{-1}$ |
| GdL bound = 99% | $1 \times 10^7$ $M^{-1}$ | $4.9 \times 10^4$ $M^{-1}$ | $1.1 \times 10^4$ $M^{-1}$ |

In one embodiment the relaxivity of the pharmaceutical composition resulting by addition of the polyarylene additive to a macrocyclic Gd-complex is at least 10% higher than that of the solution of the relevant free Gd-complex.

Advantageously, the enhanced relaxivity displayed by the pharmaceutical compositions of the invention allows reducing their diagnostically effective dose, as compared to the corresponding Gd-complexes currently used as contrast agents.

To this extent, and unless otherwise provided, the term "effective dose" or "effective amount", as used herein, refers to any amount of a pharmaceutical composition according to the invention that is sufficient to fulfil its intended diagnostic purpose(s): i.e., for example, to ex vivo visualize a biological element including cells, biological fluids and biological tissues or the in vivo diagnostic imaging of body organs, tissues or regions of a patient.

Unless otherwise indicated, with "individual patient" or "patient" as used herein we refer to a living human or animal patient, and, preferably a human being undergoing MR diagnostic assessment.

Figure 6:
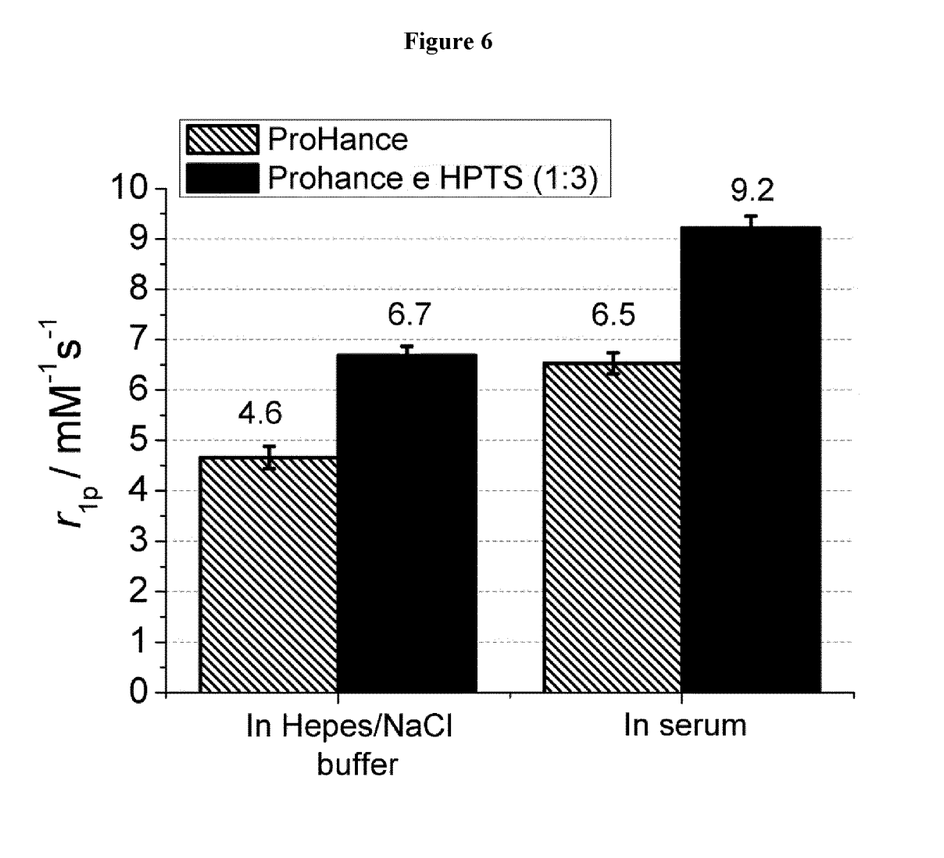
FIG. 6 shows the relaxivity of ProHance and ProHance added with HPTS (1:3 m/m ratio) in buffer and blood serum.
Figure 7:
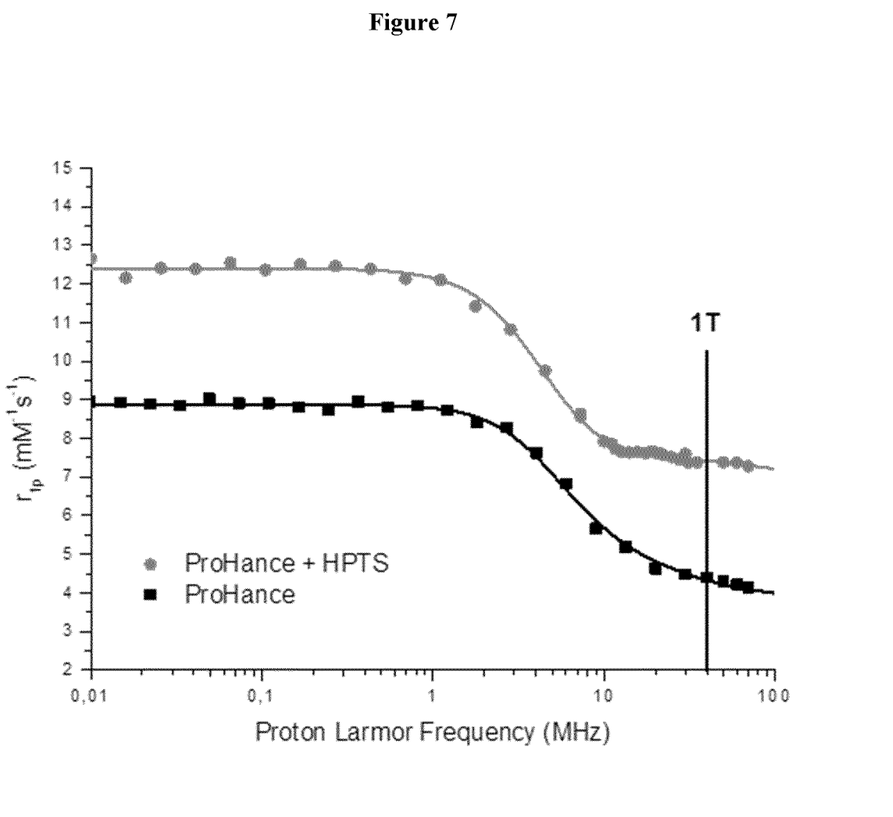
FIG. 7 shows 1H-NMRD profiles of ProHance free (■), and in the presence of 40 mM HPTS (●) ([Gd-complex]=1 mM, in Hepes/NaCl, pH=7.0).

The enhancement of relaxivity observed in saline solution with the pharmaceutical compositions of the invention comprising a macrocyclic Gd-complex and a polyarylene additive is maintained in serum (see FIG. 6) and at different (increasing) strength of the applied magnetic field (see FIG. 7).

Figure 8:
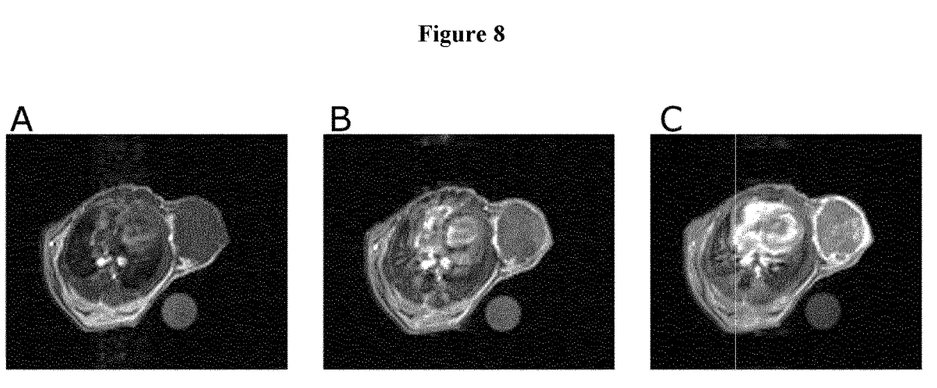
FIG. 8 shows: (A) $T_{1w}$ MR image without contrast agent, (B) $T_{1w}$ MRI image upon injection of ProHance (0.15 mmol/kg), (C) $T_{1w}$ MRI image upon injection of ProHance (0.15 mmol/kg) and HPTS (0.45 mmol/Kg) (ProHance: HPTS, 1:3).

Advantageously, moreover, the relaxivity enhancement displayed by the pharmaceutical compositions of the invention is maintained in vivo, thereby confirming the high stability of the non-covalent adduct likely formed by simple addition of the polyarylene additive to the contrast agent composition. Indeed, as shown in FIG. 8, the MRI performance of the ProHance/HPTS formulation (mean signal enhancement, Enh %, in the tumor ROI=125%) is markedly improved compared to that provided by ProHance alone (mean signal enhancement, Enh %, in the tumor ROI=53%).

Pharmaceutical compositions according to the invention may be prepared starting from an aqueous solution comprising a Gd-complex (e.g. the aqueous solution of a marketed macrocyclic tetraazacyclododecane-based contrast agents) and adding to it a water-soluble polyarylene additive, or by dissolving both water-soluble polyarylene additive and the Gd-complex of interest in an aqueous solutions, e.g. a hepes/NaCl aqueous solution ([NaCl]=0.15M, [hepes]=0.0038M, osmolarity 300 mOsm/L).

Alternatively, a suitable amount of Gd-complex can be dissolved into, an aqueous solution of the polyarylene additive. Still alternatively, a solution of the Gd-complex of interest can be admixed with an aqueous solution of the polyarylene additive.

A further aspect of the invention relates to a pharmaceutical composition as above defined for diagnostic use, in particular for use as contrast agent for the diagnostic imaging of a human or animal body organ, tissue or region, by use of the MM technique.

Preferably, the pharmaceutical composition is a contrast-producing composition and, more preferably, a MRI contrast-producing composition comprising at least one macrocyclic contrast agent and a polyarylene additive according to the invention.

More preferably the pharmaceutical composition comprises at least one Gd-complex selected between the active ingredients of Gadovist and ProHance and at least one polyarilene additive selected between HPTS and HPDS; most preferably comprises the Gd-complex Aa of ProHance and HPTS, even more preferably in a ratio of 1:3 m/m.

The invention also relates to an adduct of a macrocyclic Gd-complex with a water-soluble polyarylene additive, to an aqueous solution comprising said adduct and to its use as diagnostic agents, in particular as contrast agents, in the diagnostic imaging, preferably by use of MM technique.

More particularly, a further aspect of the invention relates to a non-covalent adduct obtainable by the interaction of a macrocyclic Gd-complex with a water-soluble polyarylene additive.

Preferably, the non-covalent adduct is between a Gd-complex selected from the group comprising:

-continued and and a polyarylene selected from the group comprising:

or physiologically acceptable salts thereof. More preferably, the adduct has an association constant Ka of at least 250 M$^{-1}$ and most preferably equal to or greater than 250 M$^{-1}$ A further aspect of the invention concerns a pharmaceutical composition for diagnostic use that comprises at least one adduct of a macrocyclic Gd-complex with a polyarylene compound in admixture with one or more physiologically carriers or excipients. Said compositions are useful in particular as MM contrast media, to provide diagnostically useful images of human or animal body organs or tissues.

More particularly, an additional aspect the invention relates to a MRI contrast medium comprising an effective amount of at least one adduct according to the invention in combination with one or more pharmaceutically acceptable carriers or excipients.

The invention further refers to a method for the in vivo or in vitro (ex vivo) imaging of a human or animal body organ, tissue or region by use of the MRI technique which comprises administering to said human or animal patient a diagnostically effective amount of a pharmaceutical composition of the invention, or contacting ex vivo samples of body organs or tissues, including cells and biological fluids of said human or animal with an effective amount of a pharmaceutical composition according to the invention, and then subjecting the administered patient or the contacted ex vivo sample to the diagnostic imaging, for example by use of the MRI technique.

More particularly, in one embodiment the invention relates to a method for the in vivo imaging of a human or animal body organ, tissue or region by use of the MM technique, that comprises the steps of:
 a) administering to said human or animal patient a diagnostically effective amount of a pharmaceutical composition of the invention;
 b) submitting the patient to a radiation frequency allowing to excite the non-zero proton spin nuclei of the active gadolinium-based substrate within the composition; and
 c) recording a MR signal from said excited nuclei.

To this extent, the expression "active gadolinium-based substrate", allowing to generate a MRI signal when subjected to an exciting radiation frequency, includes within its meanings any gadolinium-based macrocyclic complex contained in the formulation, both present in the form of a non-covalent adduct with the polyarylene additive, and as free, (i.e. non-linked) residual macrocyclic Gd-complex.

In a preferred embodiment the method is carried out on human or animal bodies suitably pre-administered with a pharmaceutical composition according to the invention.

More particularly, in one preferred embodiment the invention relates to a method for the in vivo imaging of a human or animal body organ, tissue or region by use of the MRI technique that comprises the steps of:
 a) submitting a human or animal pre-administered with an effective amount of a pharmaceutical composition according to the invention and positioned in a MM imaging system, to a radiation frequency selected to excite the non-zero proton spin nuclei of the active paramagnetic substrate of the composition; and
 b) recording a MR signal from said excited nuclei.

In another embodiment, the invention relates to a method for the in vitro (ex vivo) imaging of biological samples, including cells, biological fluids and biological tissues originating from a human or animal patient, by use of the MRI technique, that comprises contacting an effective amount of the pharmaceutical composition of the invention with the biological sample of interest and then obtaining MRI signals from said samples by use of the MM technique.

Details concerning dosages, dosage forms, modes of administration, pharmaceutically acceptable carriers, excipients, diluents, adjuvants and the like are known in the art.

The following examples further illustrate the invention.

EXAMPLES

Example 1: Preparation of a Pharmaceutical Composition Comprising a Macrocyclic Gadolinium-Based Contrast Agent and a Water-Soluble Polyarylene Additive In order to obtain the pharmaceutical composition of this invention, samples were prepared by dissolving HPTS and the Gd-complexes in hepes/NaCl water solution ([NaCl]= 0.15M, [hepes]=0.0038M, osmolarity 300 mOsm/L, pH 7.4).

For instance, for in vivo administration, 2 mL of pharmaceutical composition were prepared by dissolving 63 mg of HPTS in water solution obtained by mixing 80 µL of commercial ProHance (0.5M) with 1.920 mL of hepes/NaCl solution ([NaCl]=0.15M, [hepes]=0.0038M, osmolarity 300 mOsm/L, pH7.4). In this way a 20 mM ProHance/60 mM HPTS solution is prepared. Mice were injected with 0.15 mmoles/kg of ProHance e 0.45 mmoles/kg of HPTS (corresponding to 150-220 µL for 20-30 g mice).

For titrations, ProHance (final concentration 1 mM) wax mixed with HPTS at different concentrations (0-40 mM). pH was checked to be 7.-7.2 and, eventually adjusted by adding HCl or NaOH.

Example 2: In Vitro Determination of the Binding Parameters Ka and $R_b$

The binding parameters Ka and Rb between the investigated Gd-complexes and the polyarylene additives were calculated by using the well-established Proton Relaxation Enhancement (PRE) technique.

This method consists in measuring the variation in the longitudinal proton Relaxation Rates ($R_1=1/T_1$) of the paramagnetic solutions upon increasing the concentration of the interacting substrate. By this method, the binding parameters Ka (the affinity constant) and Rb (the relaxivity of the resulting adducts at saturation) can be determined. To this end, solutions of the Gd-complexes (1 mM) were titrated with the polyarylenes compounds and non-hydrophobic reference compounds (in the concentration range 1-40 mM, leading to the saturation of the contrast agent), at 21.5 MHz and 298 K, in Hepes/NaCl buffer solution ([hepes]=3.8 mM, [NaCl]=150 mM) at pH 7.0-7.2.

Relaxation rates were measured on a Stelar SpinMaster Relaxometer (Stelar, Mede, PV, It) operating at 21.5 MHz by means of the inversion recovery method (16 experiments, two scans). The reproducibility of the T data was ±0.5%.

Figure 5:
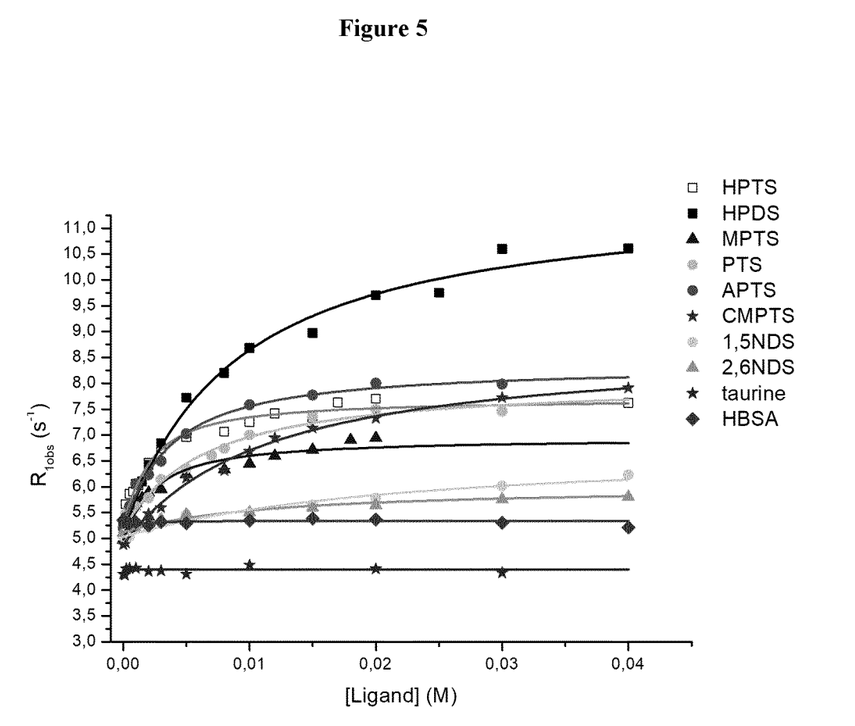
FIG. 5 shows the binding isotherms of ProHance showing the increase of relaxivity measured in the presence of increasing amounts of different polyarylic or non-arylic additives ([Gd-complex]=1 mM, in Hepes/NaCl, pH=7.0).

The least-squares fit of the $R_1$ versus substrate concentration binding isotherms (FIGS. 4 and 5) enabled us to calculate the affinity constants and the relaxivities of the adducts reported in tables 2 and 3 below.

Analysis of data was carried out by using origin 9.0 software.

The effect of the Human Serum Albumin (HSA) was investigated by measuring the relaxivity value of ProHance and Prohance/HPTS adduct (1:3) in serum (Seronorm™ SERO AS, Stasjonsveien 44, 1396 Billingstad, Norway) solution.

FIG. 4 reports the binding curves relative to the interactions of the commercial GBCAs with HPTS. The least-squares fit of the $R_1$ versus substrate concentration binding isotherms enabled us to calculate the affinity constants (Ka) and the relaxivities of the adducts (Rb) reported in table 2.

FIG. 4 and table 2 shows that the intermolecular interaction is established only when macrocyclic Gd-complexes are used. In the case of linear contrast agents Magnevist, Omniscan and MultiHance complexes no binding is observed. In the series of the three macrocyclic complexes, the affinity scale is the following: Gadovist>ProHance>Dotarem.

As clearly shown in the graph in FIG. 4, the greater is the amount of additive added to the aqueous solution of the contrast agent, the higher is the relaxation enhancement obtained. In particular, it is noteworthy that at the preferred molar ratio 1:3 of Prohance to HTPS an improvement of relaxivity of about 30% in comparison with Prohance as-such is obtained.

TABLE 2

$r_{1p}$, Ka and $R_b$ relative to the interaction of a series of GBCA with HPTS. (*)T = 25° C., $B_0$ = 21.5 MHz, pH = 7.0 ± 0.1.

Figure 2A:
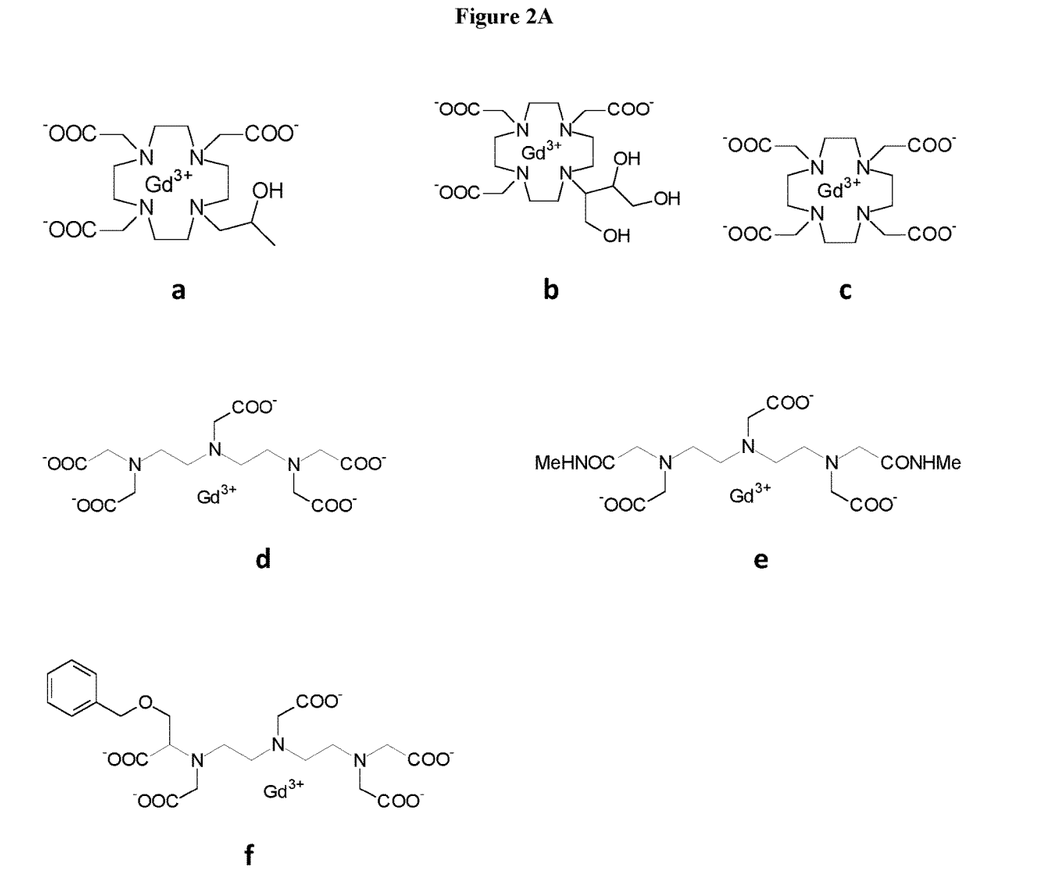
FIG. 2A shows the chemical structure of commercial gadolinium complexes: Aa) ProHance, Ab) Gadovist, Ac) Dotarem, Ad) Magnevist, Ae) Omniscan, Af) MultiHance.
Figure 2B:
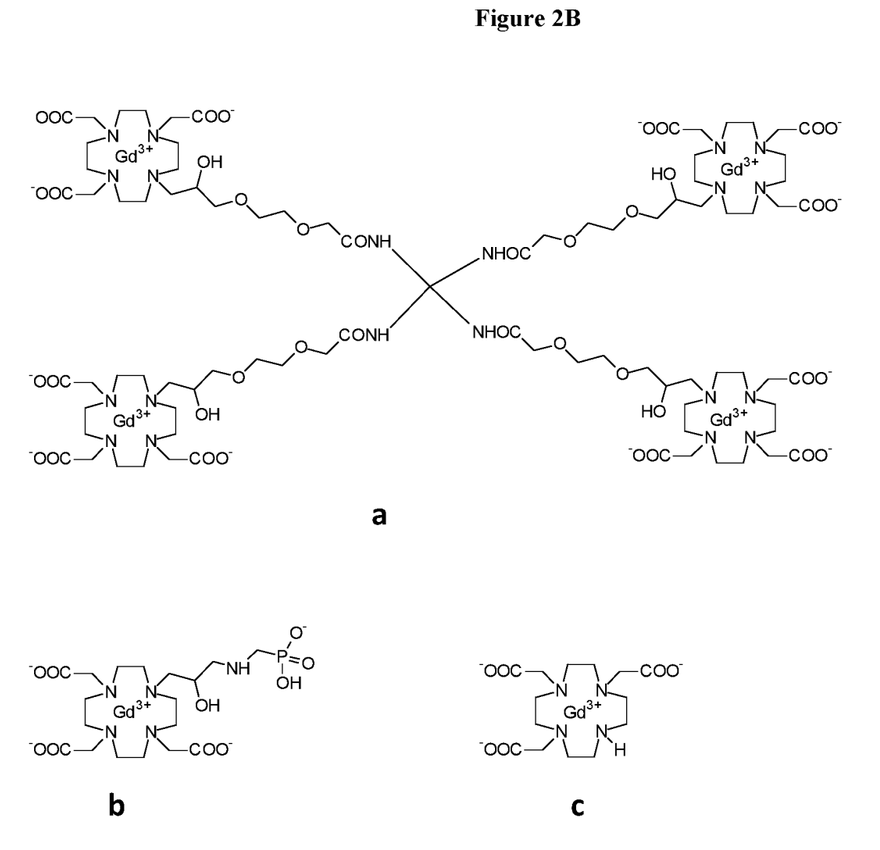
FIG. 2B shows the chemical structure of some non-marketed gadolinium complexes: Ba) tetrameric derivative of ProHance, Bb) monophosphonic derivative of ProHance, Bc) Gd-DO3A.
Figure 3A:
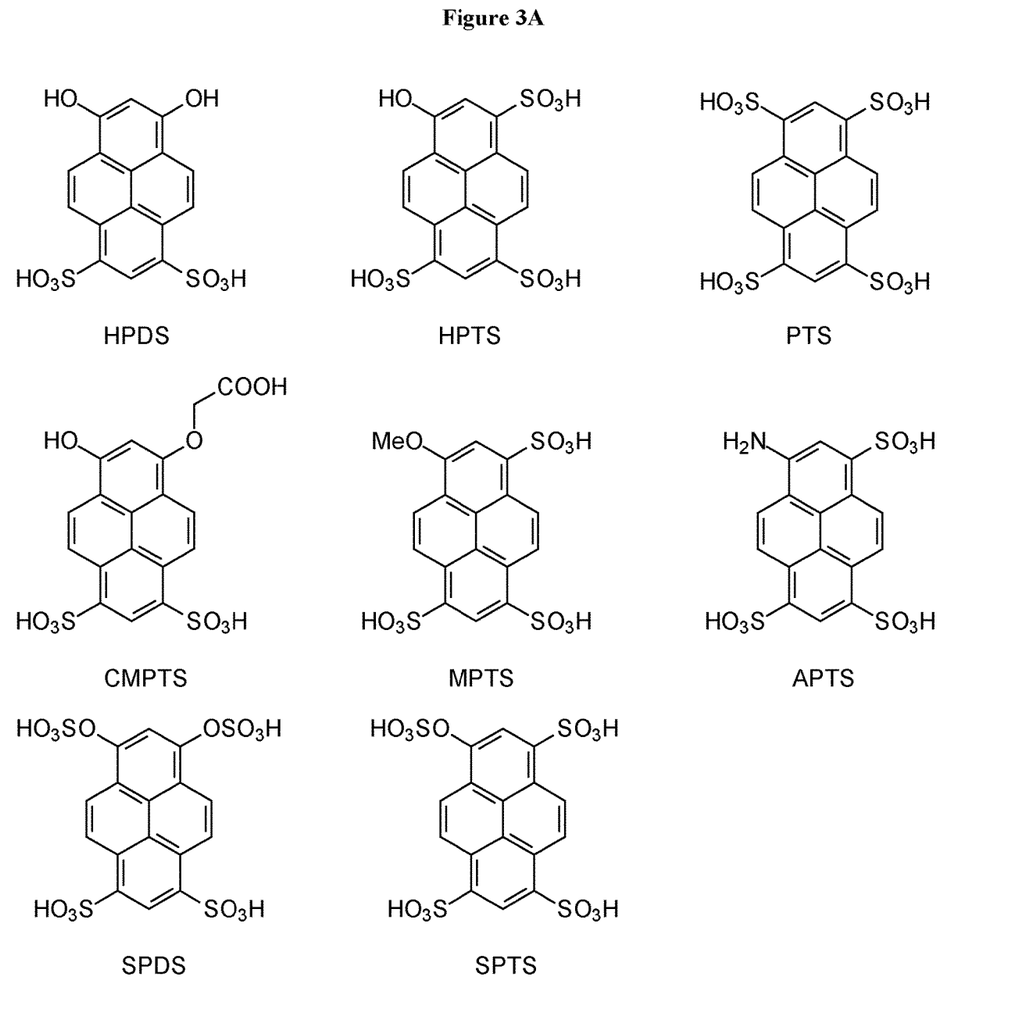
FIG. 3A shows the chemical structure of polyarylene additives according to the invention.

| | Chemical structure (FIG. 2) | $r_{1p}$ (*) (mM$^{-1}$s$^{-1}$) | Ka (M$^{-1}$) | $R_b$ (mM$^{-1}$s$^{-1}$) |
|---|---|---|---|---|
| ProHance | Aa | 4.6 | 628 | 6.9 |
| Gadovist | Ab | 5.0 | 1157 | 7.9 |
| Dotarem | Ac | 4.2 | 174 | 7.4 |
| Magnevist | Ad | No interaction | | |
| Omniscan | Ae | No interaction | | |
| MultiHance | Af | No interaction | | |
| Tetramer of ProHance | Ba | 38.4 (for tetramer) | 302 | 58.9 |
| Mono phosphonic Gd-HPDO3A | Bb | 8.4 | 359 | 12 |
| Gd-DO3A | Bc | 6.2 | 246 | 9.5 |

Some non-commercial Gd-complexes (chemical structure in FIG. 2B), with a relaxivity higher than that of ProHance, have been also investigated and their interaction with HPTS has been tested and compared with that of ProHance.

All the non-commercial complexes tested are able to interact with HPTS even if with lower affinity than ProHance. The enhancement in relaxivity obtained upon the formation of the adduct is more or less the same than that obtained for ProHance (table 2).

Other aromatic-containing structures, beside HPTS, were considered for the interaction. Results are reported in FIG. 5 and Table 3 below.

As negative control, interaction with Taurine and HBSA have been tested. No binding is present in both the titrations. These molecules have been chosen in order to exclude a direct role of sulfonic groups in the binding.

Finally, a test was performed to assess if the relaxivity enhancement observed when HPTS is added to the macrocyclic Gd-complexes in buffer is retained in blood serum solutions. As shown in FIG. 6, an enhancement of about 50% is indeed maintained both in buffer and in serum. The outstanding stability of the relaxivity enhancement in different media suggests the promising use in vivo of the pharmaceutical composition object of this invention.

TABLE 3

Ka and $R_b$ of interaction of ProHance with a series of polyarylenes and reference compounds. (*) T = 25° C., B0 = 21.5 MHz, pH = 7.0 ± 0.1.

| | Ka (M$^{-1}$) | $R_b$ (mM$^{-1}$s$^{-1}$) | $R_b/r_{1p}$ |
|---|---|---|---|
| HPDS (6,8-dihydroxypyrene-1,3 disulfonic acid) | 124 | 10.9 | 2.4 |
| HPTS (8-Hydroxypyrene-1,3,6-trisulfonic acid) | 628 | 6.9 | 1.5 |
| PTS (1,3,6,8 Pyrentetrasulfonic acid) | 177 | 7.3 | 1.6 |
| CMPTS (8-carboxymethoxypyren-1,3,6-trisulfonic acid) | 94.2 | 8.5 | 1.8 |
| APTS (8-Aminopyren-1,3,6 trisulfonic acid) | 319 | 7.6 | 1.6 |
| MPTS (8-Methoxy-1,3,6 trisulfonicpyren acid) | 514 | 6.5 | 1.4 |
| 1,5 NDS (1,5 naphthalen disulphonic acid) | 45.5 | 6.3 | 1.4 |
| 2,6 NDS (2,6 naphthalen disulphonic acid) | 94.4 | 5.4 | 1.2 |
| Taurine | No interaction | | |
| HBSA | No interaction | | |

Example 3: Determination of the NMRD Profiles

In order to investigate if the enhancement of the relaxivity is maintained at different magnetic field strength, the proton 1/T$_1$ NMRD profiles were measured at 298 K on 1 mM ProHance solutions in the absence and in the presence of 40 mM HPTS. Measurements were carried out on a fast field-cycling Stelar relaxometer over a continuum of magnetic field strengths from 0.00024 to 0.47 T (corresponding to 0.01-20 MHz proton Larmor Frequency). The relaxometer operates under computer control with an absolute uncertainty in 1/T$_1$ of ±0.1%. Additional data points in the range 21.5-70 MHz were obtained on the Stelar SpinMaster relaxometer. The concentration of the solutions used for the relaxometric characterization was determined according to a previously reported relaxometric method (Arena, F. et al, *Bioconjugate Chem.* 2011, 22, 2625-2635).

FIG. 7 displays the NMRD profiles of the macrocyclic Gd-complex Prohance in the presence of 40 mM HTPS in comparison with Prohance as-such. The analysis provides the evolution of the relaxivity of the two species as a function of the magnetic field. The obtained results show that the improvement of the relaxivity displayed by the adduct-based pharmaceutical composition is maintained over the whole range of magnetic field.

Example 4: In Vivo MRI

In vivo experiments were carried out on xenograpt murine models of cancer.

Female 10-12 weeks Balb/c mice (Charles River Laboratories, Calco, Italy) were inoculated subcutaneously in the flank with 0.1 mL of a suspension containing 5×10$^5$ TS/A mammary breast cancer cell lines (Nanni P. et al. *Clin. Exp. Metastasis* 1983, 1, 373-380). TS/A cells were grown in RPMI-medium supplemented with 10% fetal bovine serum (FBS), 2 mM glutamine, 100 U/m penicillin and 100 µg/ml streptomycin, in incubator with 5% CO$_2$, at 37° C.

For MRI acquisition, mice were anesthetized by intramuscular injection of a mixture of 20 mg/kg tiletamine/zolazepam (Zoletil 100, Virbac, Milan, Italy) 20 mg/kg plus 5 mg/kg xylazine (Rompun; Bayer, Milan, Italy). A permanent vein access was obtained by inserting a PE10 catheter into the tail vein.

MR images have been acquired, pre and post injection of GBCA, at 7.1T by using Bruker Avance 300 spectrometer equipped with a Micro 2.5 microimaging probe. Mice were injected with 0.15 mmol/Kg of ProHance followed (after 1 h when the wash-out of the GBCA was considered complete) by the injection of a mixture of ProHance and HPTS (0.15 mmol/Kg ProHance and 0.45 mmol/Kg HPTS).

Tumor volume and morphology were determined by multislices anatomical T$_{2w}$ images. A ROI was manually drawn and the slice volume was calculated. T$_{2w}$ images were acquired by using a standard T2w RARE (Rapid Acquisition with Refocused Echoes) sequence with the following parameters (TR=5000 ms, TE=5.5 ms, RARE factor=32, FOV=3.5×3.5 cm, slice thickness=1 mm, matrix 128×128).

T$_{1w}$ images were acquired by using a standard T$_{1w}$-MSME (multislice multiecho) sequence with the following parameters (TR=200 ms, TE=3.3 ms, number of average=6, FOV=3.5×3.5 cm, slice thickness=1 mm, matrix 128×128, resolution 0.273×0.273 mm/pixel). A glass tube containing a standard solution was used as internal reference. It was located in the field of view in close proximity to the mouse body. Noticeably, the relaxivity enhancement observed in vitro with ProHance and HPTS is maintained in vivo. MR images obtained on a tumor mouse model (TS/A breast cancer cells transplanted on Balb/c mice) upon injection of ProHance alone or a mixture of ProHance/HPTS (1:3 ratio) (where about 60% of ProHance is bound to HPTS) are shown in FIG. 8.

As clearly shown in the FIG. 8, the MRI performance of the ProHance/HPTS composition (mean signal enhancement, Enh %, in the tumor ROI=125%) is markedly improved in respect to that provided by ProHance alone (mean signal enhancement, Enh %, in the tumor ROI=53%), thereby confirming the in vivo stability of the adduct formed in solution and the performance of the composition of the invention.

The invention claimed is:

1. A pharmaceutical composition comprising an adduct consisting of a macrocyclic gadolinium complex (Gd-complex), or a pharmaceutical salt thereof, and a water-soluble polyarylene additive, or a pharmaceutical salt thereof, wherein the Gd-complex is tetraazacyclododecane-based with 3 or 4 carboxylic acid substituents, or a tetrameric derivative thereof, wherein the water-soluble polyarylene additive, or a pharmaceutical salt thereof, comprises 4 carbocyclic fused aromatic rings that are substituted by 2, 3, or 4 hydrophilic substituent groups selected from the group consisting of —OH, —COOH, —SO$_3$H, —OSO$_3$H, and —NH$_2$, wherein the molar ratio of macrocyclic Gd-complex to polyarylene additive ranges from 1:1 to 1:10 (m/m) and wherein the macrocyclic Gd-complex has an association constant Ka for the polyarylene additive of at least 250 M$^{-1}$.

2. The pharmaceutical composition according to claim 1 wherein the Gd-complex is selected from the group consisting of:

3. A pharmaceutical composition according to claim 1, wherein the Ka is at least 350 M$^{-1}$.

4. A pharmaceutical composition according to claim 1, wherein the polyarylene compound is selected from the group consisting of:

5. A pharmaceutical composition according to claim 1, wherein the Gd-complex is the compound of formula:

and the polyarylene additive is HPTS or HPDS.

6. The pharmaceutical composition according to claim 5, wherein the Gd-complex is the compound of formula Aa and the polyarylene additive is HPTS.

7. The pharmaceutical composition according to claim 1, wherein the molar ratio of macrocyclic Gd-complex to polyarylene additive is 1:3.

8. The pharmaceutical composition according to claim 1, wherein the Ka is at least 450 M$^{-1}$.

9. The pharmaceutical composition according to claim 1, wherein the Ka is at least 600 M$^{-1}$.

10. The pharmaceutical composition according to claim 1, wherein the molar ratio of macrocyclic Gd-complex to polyarylene additive ranges from 1:1 to 1:5.

* * * * *